United States Patent [19]

Fracasiu

[11] Patent Number: 4,677,090
[45] Date of Patent: Jun. 30, 1987

[54] LIQUID CATALYST FOR HYDROCARBON CONVERSION REACTIONS

[75] Inventor: Dan A. Fracasiu, Flemington, N.J.

[73] Assignee: Exxon Research and Engineering Company, Florham Park, N.J.

[21] Appl. No.: 818,168

[22] Filed: Jan. 13, 1986

Related U.S. Application Data

[63] Continuation of Ser. No. 619,076, Jun. 11, 1984, abandoned.

[51] Int. Cl.$^4$ .................. B01J 31/04; B01J 31/02
[52] U.S. Cl. ................... 502/168; 502/150; 502/172; 585/470
[58] Field of Search .................. 502/163, 172, 150

[56] References Cited

U.S. PATENT DOCUMENTS

| | | | |
|---|---|---|---|
| 2,090,905 | 8/1938 | Stevens et al. | 502/172 X |
| 2,981,772 | 4/1961 | Holzman | 502/150 X |
| 4,038,212 | 7/1977 | Brockington et al. | 502/168 |
| 4,347,384 | 8/1982 | Fields | 502/150 X |
| 4,525,470 | 6/1985 | Kohl | 502/168 X |
| 4,585,750 | 4/1986 | Farcasiu | 502/168 X |

Primary Examiner—Patrick P. Garvin
Attorney, Agent, or Firm—Jay Simon

[57] ABSTRACT

A liquid catalyst for hydrocarbon conversion reactions and a method for reacting hydrocarbons employing such catalyst is provided by the present invention. The liquid catalyst includes a strong liquid acid such as sulfuric acid or trifluoromethanesulfonic acid and an ion-stabilizing agent such as hexafluoroisopropanol or trifluoroacetic acid. The liquid catalyst has a significantly higher Bronsted acidity than the strong liquid Bronsted acid alone. When the liquid catalyst is used to catalyze the transalkylation of alkylbenzene, for example, the rate of transalkylation is from 2 to 3 times greater than using the strong liquid acid alone.

6 Claims, No Drawings

LIQUID CATALYST FOR HYDROCARBON CONVERSION REACTIONS

This application is a Rule 60 continuation of Ser. No. 619,076 filed June 11, 1984 and now abandoned.

BACKGROUND OF THE INVENTION

This invention is concerned with liquid acid catalysts for hydrocarbon reactions and a method for reacting hydrocarbons employing such catalyst.

In the past hydrocarbon conversion reactions such as alkylations, acylations, rearrangements, and isomerizations have been carried out in the presence of strong Lewis acids or strong Bronsted acids. A Lewis acid is a compound in which the normal electronic grouping about the central atom can accept an electron pair from a Lewis base which is any compound capable of donating an electron pair. Such Lewis acids include fluorides, chlorides, and bromides of aluminum, zinc, titanium, zirconium, antimony and iron. Bronsted acidity, on the other hand, reflects the ability of a protonic acid to transfer a proton to a base. Bronsted acids suitable as catalysts for hydrocarbon conversion reactions include strong protonic acids such as liquid sulfuric acid, hydrogen fluoride, phosphoric acid and trifluoromethanesulfonic acid. Generally these protonic acids have an $H_o$ value on the Hammett scale of $-11$ or less, and they have been applied in organic syntheses for a variety of reactions, including the alkylation of arenes with alkenes, alcohols, and esters; transalkylation of arenes with polyalkylbenzenes; acylation, sulfonation, and nitration of aromatic compounds; acylation of alkenes; and hydration of lower olefins. Common to all these acid-catalyzed reactions is the formation of carbocations as intermediates.

The effectiveness of such Lewis acid and Bronsted acid catalysts for hydrocarbon conversions is directly related to the acidity of the catalyst material toward the hydrocarbon substrate. Any modification which increases the acidity of the acid will result in an increase of its catalytic activity.

It has now been found that the acidity of a strong liquid Bronsted acid can be enhanced by adding to it an ion-stabilizing agent to form a liquid catalyst with increased catalytic activity.

SUMMARY OF THE INVENTION

The catalyst product of the invention is a combination of a liquid strong or super acid, such as liquid sulfuric or trifluoromethanesulfonic acid, and an ion-stabilizing agent such as trifluoroacetic acid or hexafluoroisopropanol which are also liquids. The resulting combination is a liquid catalyst. The liquid catalyst can also be present as a solution in an appropriate solvent. The acidity toward hydrocarbons of the so-formed liquid catalyst is significantly higher than that of the original acid such that the liquid combination will protonate a standard base, hexamethylbenzene, to a much greater degree than the original acid for the same acid to base ratio. The ion-stabilizing agent alone will not protonate hexamethylbenzene.

The liquid catalyst is useful as a catalyst for hydrocarbon conversion reactions such as those described above in which carbocations are formed as intermediates. It has been found that by employing the catalyst in an aromatic transalkylation reaction, for example, the rate of transalkylation is from about 2 to 3 times faster than the same reaction catalyzed by the strong liquid acid alone.

DETAILED DESCRIPTION OF THE PREFERRED EMBODIMENTS

The acid catalyst of this invention comprises the combination of a liquid acid, such as sulfuric or trifluoromethanesulfonic acid, and at least one ion-stabilizing agent such as trifluoroacetic acid (TFA) or hexafluoroisoproponol (HFIP). An ion-stabilizing agent as used herein is a highly polar substance which can interact with ions by a mechanism such as solvation to make the ions more stable. It is considered that the ion-stabilizing agent interacts specifically with the anion resulting from the acid upon proton transfer to a base, i.e. the hydrocarbon.

Acidity is defined, manifested, and measured in relation to a base. The strength of an acid can be evaluated by the extent to which a standard base is protonated by the acid for a given initial acid/base ratio. Aromatic hydrocarbons are convenient standard bases for evaluation of superacidic strength. The amount of protonate aromatic present at equilibrium can be determined by carbon-13 nuclear magnetic resonance, hereafter $^{13}$C-NMR.

The acidity of the liquid catalyst of this invention is evaluated by the degree of protonation of hexamethylbenzene (HMB) as the standard base, according to equation (I) below.

$$C_6Me_6 + [H^+] \rightleftharpoons C_6Me_6H^+ \qquad (I)$$

For the purpose of equation (I), $[H^+]$ represents any acid (source of proton) that can transfer its proton to a base, in this case HMB. When HMB is dissolved in a non-protonic medium such as chloroform (deuterated), liquid sulfur dioxide, sulfuryl chloride fluoride, two signals appear in the $^{13}$C-NMR spectra attributable to the carbon atom attached to the benzene ring of HMB and the aromatic carbon atoms. The same kind of spectrum is obtained when an ion-stabilizing agent such as trifluoroacetic acid is contacted with HMB, that is, HMB is not protonated. However, when HMB is dissolved in a super acid such as fluorosulfonic acid and antimony pentafluoride ($FSO_3H$-$SbF_5$) or a large excess of trifluoromethanesulfonic acid ($CF_3SO_3H$), a multiplicity of signals are exhibited at low temperature, which can be assigned to protonated HMB. These signals are time-averaged to 50° to 60° C., to give two signals at locations (chemical shifts) different from those observed for non-protonated HMB.

The degree of protonation of HMB in other acidic media, including the liquid catalyst according to the invention, can be determined by interpolation of the time-averaged $^{13}$C-NMR spectra of HMB in those media, between the spectrum of HMB in a non-acidic solution and the time-averaged spectrum of HMB in a super acid in which HMB is fully protonated such as fluorosulfonic acid and antimony pentafluoride ($FSO_3H$-$SbF_5$) or a large excess of trifluoromethanesulfonic acid ($CF_3SO_3H$).

Acids which are stronger than neat trifluoromethanesulfonic acid cannot be differentiated by HMB, since they all protonate HMB completely (leveling effect). Conversely, acids that are significantly weaker than, for example, sulfuric acid do not protonate HMB at all, that is they are not acidic relative to HMB. However, the addition of an ion-stabilizing agent to such weaker acids may increase their acidity to the degree that they will protonate HMB.

The liquid catalyst of this invention can be prepared by mixing the liquid acid with the ion-stabilizing agent. To employ the catalyst, the reactant or reactants to be converted are contacted with the so-formed liquid catalyst under reaction conditions to effect the reaction. Alternatively, the ion-stabilizing agent can be mixed with the reactants to be converted, then the mixture thus formed is contacted with the liquid acid under reaction conditions to effect the reaction. The liquid catalyst can also be formed in solution by combining the components in a solvent such as chloroform, dichloromethane or other solvent which is non reactive with the liquid acid, ion stabilizers or any reactant used therewith.

Generally the amount of ion-stabilizing agent should constitute from 10% to 700% by weight of the liquid acid or stated otherwise, the weight ratio of ion-stabilizing agent to the liquid acid is from about 0.1 to 1 to 7 to 1.

The composite of liquid acid and ion-stabilizing agent, according to the invention, is useful as a catalyst for carbocationic (acid-catalyzed) processes such as the transalkylation of arenes with polyalkylbenzenes. The liquid catalyst has a better activity, that is, promotes a higher reaction rate, than the liquid acid alone. The composite catalyst is useful in all those carbocationic organic reactions for which its liquid acid component has been previously used.

When using the liquid catalyst for hydrocarbon conversion reactions such as the transalkylation of p-di-tert-butylbenzene with toluene the rate is about 2 to 3 times faster than when using the liquid acid alone.

EXAMPLE 1

This Example demonstrates the inability to protonate HMB of each of two ion-stabilizing agents, trifluoroacetic acid (TFA), and hexafluoroisopropanol (HFIP) compared to a standard strong liquid acid, trifluoromethanesulfonic acid, and demonstrates the application of $^{31}$C-NMR to calculate the degree of protonation of HMB.

In this and in the following examples, the HFIP was dried on molecular sieves 3A, the chloroform was distilled from phosphorus pentoxide, and the TFA was mixed with 10% of its anhydride, boiled under reflux for 15 minutes, the fractionally distilled. To the distilled acid, 0.5–1% anhydride was added. These materials were stored under nitrogen in a dry-box and the samples were prepared inside the same dry-box. Distilled sulfuryl chloride fluoride ($SO_2ClF$) was stored in a glass pressure vessel inside the dry-box, and it was cooled before opening for preparation of samples. Anhydrous sulfur dioxide ($SO_2$) purchased and stored in a steel container ("Lecture bottle") was expanded slowly into a vacuum line through a column of phosphorus pentoxide 7.5 cm long, and was condensed into an 8 mm O.D. glass tube containing the other components cooled in liquid nitrogen. The tube was then sealed off and used for $^{13}$C-NMR analysis. The tubes with samples containing $SO_2ClF$, were filled inside the dry-box, then were connected to the vacuum line and sealed off as well. Contamination by air and moisture was carefully avoided during NMR analyses.

(a) Hexamethylbenzene (0.09 g) was dissolved in a mixture of HFIP (1.2 mL) and chloroform (0.2 mL). The $^{13}$C-NMR spectrum of the solution had signals at 132.84 ppm (aromatic carbon) and 14.90 ppm (methyl carbon) ppm from external/coaxial tetramethylsilane. No evidence of protonation of HMB was shown.

(b) Hexamethylbenzene (0.08 g) was dissolved in 1 mL of a 75:25 (v:v) mixture of TFA and chloroform. $^{13}$C-NMR signals for HMB were recorded at 131.81 ppm and 15.20 ppm indicating no protonation of HMB.

(c) Hexamethylbenzene (0.063 g) was dissolved in a mixture of $SO_2ClF$ (0.8 mL) and chloroform (0.2 mL). The $^{13}$C-NMR signals for HMB were recorded at 131.54 ppm and 15.60 ppm.

(d) Hexamethylbenzene (0.120 g) was dissolved in a mixture of $SO_2$ (1.65 mL) and chloroform (0.10 mL). The $^{13}$C-NMR signals for HMB were recorded at 133.18 ppm and 15.80 ppm.

(e) Hexamethylbenzene (0.162 g, 1.006 mmol) was dissolved in 2 mL of trifluoromethanesulfonic acid. The $^{13}$C-NMR spectrum of protonated HMB exhibited 7 signals at $-60°$ C.: 192.3 (2 carbons), 190.5 (1 carbon) 138.5 (2 carbons) and 56.0 (1 carbon) for the ring carbon atoms, and 23.3 (3 carbons), 19.7 (2 carbons), and 13.6 ppm (1 carbon) for the methyl carbon atoms. These became time-averaged at $+50°$, to exhibit 2 signals, at 151.9 and 19.09 ppm, for the ring and methyl carbons, respectively.

Comparison of the peak positions (chemical shifts), in cases (a) and (b) with the chemical shifts in cases (c) and (d) (non-acidic solvents) shows that both TFA and HFIP alone do not protonate HMB. Comparison between the peak position (chemical shifts) in case (e) and in cases (a) to (d), shows the effect of protonation of HMB by trifluoromethanesulfonic acid.

EXAMPLE 2

This Example demonstrates the protonation of HMB by trifluoromethanesulfonic acid or sulfuric acid and demonstrates the application of $^{13}$C-NMR to calculate the degree of protonation of HMB.

(a) Hexamethylbenzene (0.061 g., 0.375 mmol) was mixed with 1 mL $SO_2ClF$ and 0.2 mL chloroform; trifluoromethanesulfonic acid (0.024 g, 1.36 mmol) was added. $^{13}$C-NMR signals at temperatures of 50° to 60° C. were located at 138.7–139.6 and 16.72 to 16.96 ppm. Interpolation using the values in Example 1(c) and (e) indicated 36±4% protonation of HMB at a molar ratio of trifluoromethanesulfonic acid to HMB of 3.62 to 1.

(b) Sulfuric acid was obtained by mixing 10.05 mL of 96% sulfuric acid with 10.0 mL of 17.4% oleum. Titration of the resulting acid with sodium hydroxide gave 38.36 equivalents of acid per liter, which corresponds to 4.8% free $SO_3$ in the acid. Hexamethylbenzene (0.123 g, 0.76 mmol) was mixed with 0.30 mL of this sulfuric acid (5.76 mmol), 0.10 mL chloroform, and 1.8 mL $SO_2$. $^{13}$C-NMR signals at 55° were located at 133.64 and 16.13 ppm. Interpolation using the values in Example 1(d) and 1(e) indicated 6±3.5% protonation of HMB at a 7.58:1 molar ratio of sulfuric acid to HMB.

EXAMPLE 3

This example demonstrates the effect of hexafluoroisopropanol (HFIP) upon the protonation of HMB by trifluoromethanesulfonic acid and sulfuric acid. It also demonstrates the increase in protonation with an increase in the ratio of acid to HMB.

(a) Hexamethylbenzene (0.163 g., 1.01 mmol) was mixed with trifluoromethanesulfonic acid (0.55 g, 3.67 mmol), HFIP (2.2 mL) and chloroform (0.10 mL). $^{13}$C-NMR chemical shifts at 50° C. (143.78, 17.17 ppm)

interpolated using the values in Example 1(a) and 1(e) indicated 56±2% protonation at a 3.63:1 molar ratio of trifluoromethanesulfonic acid to HMB which is an improvement in a protonation of from 35% to 81% over the strong liquid acid alone as in example 2(a).

(b) A sample was prepared as in Example 3(a), except that 0.75 g (5.0 mmol) trifluoromethanesulfonic acid was used. The $^{13}$C-MNR chemical shifts at 50° C. (148.06, 18.15 ppm) indicated 79+1.5% protonation at a 4.96:1 molar ratio of trifluoromethanesulfonic acid to HMB.

(c) A sample was prepared as in Example 3(b), except that sulfuric acid (0.265 mL, 5.03 mmol) was used instead of trifluoromethanesulfonic acid. The $^{13}$C-NMR chemical shifts at 55° C. (137.00, 15.71 ppm) indicated 20.5±1.5% protonation at a 5.02:1 molar ratio of sulfuric acid to HMB which is an improvement in protonation of from 128% to 820% over the strong liquid acid alone as in Example 2(b) even though the acid to base ratio was lower.

(d) A sample was prepared as in Example 3(c) except that 0.40 mL (7.60 mmol) of sulfuric acid was used. The $^{13}$C-NMR chemical shifts at 55° C. (139.50, 16.18 ppm) indicated 33.0±2% protonation at a 7.58:1 molar ratio of sulfuric acid to HMB.

EXAMPLE 4

This example demonstrates the effect of trifluoroacetic acid (TFA) upon the protonation of HMB by trifluoromethanesulfonic acid and sulfuric acid.

(a) A sample was prepared as in Example 3(a), except that the solution contained 1.5 mL TFA and 0.5 mL chloroform. The chemical shifts at 50° C. (145.18, 17.90 ppm) interpolated using the values in Example 1(b) and 1(e) indicated 68±1.5% protonation at a 5.03:1 molar ratio of trifluoromethanesulfonic acid to HMB.

(b) A sample was prepared as in Example 4(a), except that sulfuric acid (0.265 mL, 5.03 mmol) was used. The chemical shifts at 50° C. (132.63, 15.66 ppm) indicated 8.0±4% protonation at a 5.03:1 molar ratio of sulfuric acid to HMB.

(c) A sample was prepared as in Example 4(b), except that 0.40 mL, (7.60 mmol) of sulfuric acid was used. The $^{13}$C-NMR chemical shifts at 50° C. (135.5, 16.37 ppm) indicated 24±6% protonation at a 7.58:1 molar ratio of sulfuric acid to HMB.

EXAMPLE 5

This and the following examples illustrate the increase in the rate of transalkylation of p-di-tert-butylbenzene with toluene by using the catalyst composite of the invention.

In this Example, the rate of transalkylation of p-di-tert-butylbenzene with toluene, catalyzed by sulfuric acid, was ascertained.

A reactant mixture was prepared by dissolving 3.581 g (18.816 mmol) p-di-tert-butylbenzene (p-DTBB) in 10 mL (8.65 g, 93.9 mmol) of toluene and 1.68 mL (1.27 g., 6.89 mmol) of n-tridecane as an integration standard. The liquids were dried by storage over 3A molecular sieves, while p-DTBB was dried over phosphorus pentoxide, under vacuum, for 20 hrs. The reactant mixture was analyzed after dilution with 50 volumes of pentane by gas-liquid chromatography (GLC) on a 10 ft 10% SP-1000 column at 120° C.

Sulfuric acid (0.3 mL) was placed in a 5 mL round-bottomed flask with a Teflon-coated magnetic stirring bar, and capped with a rubber septum. The flask was placed in a thermostated bath at 27.0°±0.2° C. and stirred for 20 min. for temperature equilibration. The reactant mixture (1.0 mL), pre-equilibrated at the same temperature was injected with a syringe through the septum. Samples (0.02 mL each) were withdrawn with a syringe from the hydrocarbon layer during the reaction, diluted with pentane (1 mL) and analyzed by GLC as above. Besides the components of the starting mixture, the solution contained tert-butylbenzene and p-tert-butyltoluene as major products, m-tert-butyltoluene and m-di-tert-butylbenzene as minor products, and traces of benzene. These products were identified by comparison of their GLC behavior with authentic materials. The progress of the reaction was followed by the disappearance of p-DTBB, through conversion to the products.

EXAMPLE 5(a)

In this Example the experiments of Example 5 were repeated, except that the acid was replaced by a mixture of 0.3 mL sulfuric acid and 0.3 mL trifluoroacetic acid (TFA).

EXAMPLE 5(b)

In this Example the experiments of Example 6 were repeated, except that the composite catalyst was made with 0.3 mL of HFIP instead of TFA. The results of Examples 5, 5a & 5b are shown in Table 1 below.

TABLE 1

| | | Transalkylation of p-di-tert-Butylbenzene with Toluene Measured by the Amount of Unreacted p-DTBB Remaining | | | | | | | |
|---|---|---|---|---|---|---|---|---|---|
| No. | Catalyst | 0.5 hr. | 1 hr. | 2 hr. | 2.5 hr. | 3.5 hr. | 5 hr. | 7 hr. | 23 hr. |
| 5 | $H_2SO_4$ | 88 | 85 | 81 | — | 78 | 76 | 75 | 66 |
| 5a | $H_2SO_4$/TFA | 65 | 60 | 53 | — | 48 | 43 | 41 | 35[a] |
| 5b | $H_2SO_4$/HFIP | 46 | 40 | (35)[b] | 32.5 | 30 | 28 | 26 | 21.5[c] |

[a]22.5h; [b]interpolated value; [c]23.5 h

As Table 1 shows, after the first hour the reaction using the H$_2$SO$_4$/TFA Catalyst was over twice as fast as the reaction catalyzed by H$_2$SO$_4$ alone and the reaction using the H$_2$SO$_4$/HFIP catalyst was five times as fast. At the end of 5 hours the reaction using the H$_2$SO$_4$/TFA Catalyst was still proceeding twice as fast as the reaction catalyzed by H$_2$SO$_4$ alone and the reaction using H$_2$SO$_4$/HFIP catalyst was over three times as fast.

EXAMPLE 6

This Example demonstrates that the ion-stabilizing agent is not a catalyst by itself in the transalkylation.

The experiment of Example 7 was repeated, except that the composite catalyst was replaced by 0.6 mL of TFA. No reaction was observed for up to 24 hours of stirring.

The acidity of strong liquid protonic acids other than trifluoromethanesulfonic acid and sulfuric acid can be enhanced by employing an ion stabilizing agent according to the invention therewith. Such acids may be useful as catalysts for hydrocarbon conversion reactions or for various other liquid acid related utilities. These acids include those liquid protonic acids which are not so highly acidic that they protonate the ion-stabilizing agent itself nor so weakly acidic that they act as a base for the ion-stabilizing agent and are themselves protonated.

What is claimed is:

1. A liquid catalyst comprising a protonic acid selected from the group consisting of trifluoromethanesulfonic acid and sulfuric acid and a hexafluoroisopropanol ion stabilizing agent.

2. The catalyst of claim 1 wherein the protonic acid is sulfuric acid.

3. The catalyst of claim 1 wherein the protonic acid is trifluoromethanesulfonic acid.

4. The catalyst of claim 1 wherein the weight ratio of ion stabilizing agent to protonic acid is from about 0.1 to 1 to 7.0 to 1.

5. The process of claim 1 wherein the catalyst further comprises a solvent.

6. A method for increasing the acidity of a liquid protonic acid selected from the group consisting of trifluoromethanesulfonic acid and sulfuric acid which comprises adding to the acid hexafluoroisopropanol.

* * * * *